United States Patent
Oberle et al.

(10) Patent No.: US 7,495,355 B2
(45) Date of Patent: Feb. 24, 2009

(54) METHOD AND SYSTEM FOR PROVIDING AUXILIARY POWER FOR ANESTHESIA DELIVERY AND PATIENT MONITORING

(75) Inventors: Michael D. Oberle, Middleton, WI (US); John C. Probert, Madison, WI (US); Larry E. Alm, Fitchburg, WI (US)

(73) Assignee: The General Electric Company, Schenectady, NY (US)

( * ) Notice: Subject to any disclaimer, the term of this patent is extended or adjusted under 35 U.S.C. 154(b) by 633 days.

(21) Appl. No.: 11/057,813

(22) Filed: Feb. 14, 2005

(65) Prior Publication Data
US 2006/0181153 A1 Aug. 17, 2006

(51) Int. Cl.
*H02J 3/38* (2006.01)
(52) U.S. Cl. ...................................... 307/19
(58) Field of Classification Search ................ 307/19, 307/23
See application file for complete search history.

(56) References Cited

U.S. PATENT DOCUMENTS

| | | | |
|---|---|---|---|
| 4,141,354 A * | 2/1979 | Ismach | 128/204.28 |
| 6,476,519 B1 * | 11/2002 | Weiner | 307/66 |
| 7,105,949 B2 * | 9/2006 | Wang et al. | 307/51 |
| 7,252,088 B1 * | 8/2007 | Nieves-Ramirez | 128/204.18 |

* cited by examiner

*Primary Examiner*—Stephen W Jackson
*Assistant Examiner*—Daniel Cavallari
(74) *Attorney, Agent, or Firm*—Andrus, Sceales, Starke & Sawall, LLP

(57) ABSTRACT

The present invention is a method and system for providing auxiliary power to an integrated anesthesia delivery and patient monitoring system. When AC main power is unavailable or inadequate to power a patient monitoring device of the integrated system, DC power from a battery in an anesthesia machine of the integrated system provides power to the patient monitoring device through a DC power connection. Distribution of the battery power is controlled by a first, normally closed solid state switch in the anesthesia machine and a second, normally open solid state switch in the patient monitoring device. The battery is also configured to provide DC power to the anesthesia machine when AC mains power is unavailable to the anesthesia machine. The method and system utilizes required DC auxiliary power from the anesthesia machine to provide DC auxiliary power to the other devices.

26 Claims, 3 Drawing Sheets

METHOD AND SYSTEM FOR PROVIDING AUXILIARY POWER FOR ANESTHESIA DELIVERY AND PATIENT MONITORING

FIELD OF THE INVENTION

The invention relates to the field of patient monitoring. More particularly, the invention relates to a power substation for use with an integrated anesthesia delivery and patient monitoring system.

BACKGROUND OF THE INVENTION

In an operating room environment, anesthesia delivery systems are required to have backup power in the event of loss of AC mains power, while patient monitoring systems are not required to provide such backup power. When AC mains is lost, the clinician is put in an anxious situation since the anesthesia delivery system remains operational without any patient monitoring data. Clinicians would prefer to have the complete integrated anesthesia delivery and patient monitoring system remain powered when the AC mains is lost or interrupted.

FIG. 1 depicts a block diagram of an integrated anesthesia and patient monitoring system of the prior art. In this prior art model, an anesthesia machine 10 includes a power supply 14, a battery 16, a DC to DC converter 18 and an anesthesia machine load 20. An AC mains 12 power supply provides power to the anesthesia machine 10. A patient monitoring device 30 includes a power supply 34, a DC to DC converter 36 and a patient monitor load 38. An AC mains 32 power supply also powers the patient monitoring device 30.

In operation, when the AC main 12 power supply is present, the anesthesia machine 10 is powered by the AC main 12 power supply. When no AC main 12 power supply is available, or when the AC main 12 power supply falls below a functional operation level, the power supply 14 is disabled and the battery 16 powers the anesthesia machine load 20 through the DC to DC converter 18. The anesthesia machine 10 will receive power from the battery 16 until the battery 16 is depleted, or until the AC main 12 power is reestablished.

The patient monitoring device 30 will only operate if the AC main 32 is providing power to the power supply 34, thus powering the patient monitor load 38 through the DC to DC converter 36. Upon failure of the AC main 32 power supply, the patient monitoring device 30 will fail.

Current solutions to the interruption of operation of the patient monitoring device upon the loss of AC power include a patient monitoring power supply system with a battery that provides backup when AC mains is lost, and an anesthesia delivery system power supply that provides all power (when AC mains is available or the system is on battery) to the patient monitoring system such that the patient monitoring system does not have its own AC main supply. These solutions are oftentimes quite expensive.

SUMMARY OF THE INVENTION

The present invention is a method and system for providing auxiliary power to an integrated anesthesia delivery and patient monitoring system. When AC main power is unavailable or inadequate to power a patient monitoring device of the integrated system, DC power from a battery in an anesthesia machine of the integrated system provides power to the patient monitoring device through a DC power connection. Distribution of the battery power is controlled by a first solid state switch in the anesthesia machine and a second solid state switch in the patient monitoring device. The battery is also configured to provide DC power to the anesthesia machine when AC mains power is unavailable to the anesthesia machine. The method and system utilizes required DC auxiliary power from the anesthesia machine to provide DC auxiliary power to the other devices.

In one aspect of the present invention, a system for providing auxiliary power to an integrated anesthesia delivery and patient monitoring system comprises an anesthesia machine, which includes a battery and a first solid state switch, the patient monitoring device, which includes a second solid state switch, and a DC power connection coupling the anesthesia device and the patient monitoring device, wherein when an AC mains is unavailable to the patient monitoring device, the second solid state switch closes, such that the battery provides power to the patient monitoring device through the DC power connection.

The anesthesia machine further comprises a first power switch and a first DC/DC converter, wherein when the AC mains is unavailable to the anesthesia machine, the battery provides power to an anesthesia machine load through the DC/DC converter. The patient monitoring device further comprises a second power switch and a second DC/DC converter, wherein when the AC mains is unavailable to the patient monitoring device, the battery provides power to a patient monitoring device load through the second DC/DC converter. When the AC mains drops below a predetermined level, the second power supply is disabled and the second solid state switch closes, such that the battery provides power to the patient monitoring device through the DC power connection.

The patient monitoring device is powered by the battery for a predetermined time period, and after the predetermined time period, the anesthesia machine will open the first solid state switch, such that the patient monitoring device is disabled, and an alarm sounds when one of the anesthesia machine and patient monitoring device is receiving power from the battery.

The battery may be externally coupled to the anesthesia machine, the patient monitoring device is any device capable of receiving auxiliary power, and when the AC mains is available and above a predetermined level, the battery provides no DC power to the anesthesia machine and the patient monitoring device, and the battery is recharged.

In another aspect of the present invention, a method of providing auxiliary power to a carestation comprises monitoring a patient monitoring device for an AC mains failure, closing a second solid state switch when the AC mains failure is detected, such that the first solid state switch and the second solid state switch are connected with a DC power connection, wherein the first solid state switch is configured in an anesthesia machine and the second solid state switch is configured in the patient monitoring device, and supplying the patient monitoring device with DC power from a battery in the anesthesia machine through the DC power connection.

The supplying step further comprises supplying an anesthesia machine load of the anesthesia machine with DC power through a first DC/DC converter when a first power switch detects the AC mains failure, wherein the supplying step further comprises supplying a patient monitoring device load of the patient monitoring device with DC power through a second DC/DC converter when a second power switch detects the AC mains failure, and wherein the detecting step further comprises detecting a drop in the AC main below a predetermined level.

When the AC main drops below a predetermined level, the method further comprises disabling the second power supply and closing the second solid state switch such that the battery provides power to the patient monitoring device through the DC power connection, and when the patient monitoring device is powered by the battery for a predetermined time period, the method further comprises the anesthesia machine opening the first solid state switch, such that the patient monitoring device is disabled after the predetermined time period.

The method further comprises activating an alarm when one of the anesthesia machine and patient monitoring device is receiving power from the battery, and coupling the battery externally to the anesthesia machine, wherein the patient monitoring device is any device capable of receiving auxiliary power and when the AC mains is available and above a predetermined level, the method further comprises providing no DC power from the battery to the anesthesia machine and the patient monitoring device and recharging the battery.

In yet another aspect of the present invention, a system for providing auxiliary power to a carestation comprises means for monitoring a patient monitoring device for an AC mains failure, means for connecting an anesthesia machine and the patient monitoring device when the AC mains failure is detected including a first solid state switch and a second solid state switch, such that the first solid state switch and the second solid state switch are connected with a DC power connection, wherein the first solid state switch is configured in the anesthesia machine and the second solid state switch is configured in the patient monitoring device, and means for supplying the patient monitoring device with DC power from a battery in the anesthesia machine through the connecting means.

The supplying means further comprise means for supplying an anesthesia machine load of the anesthesia machine with DC power through a first DC/DC converter when the monitoring means detects the AC mains failure, wherein the supplying means further comprises means for supplying a patient monitoring device load of the patient monitoring device with DC power through a second DC/DC converter when the monitoring means detects the AC mains failure, and wherein the monitoring means further comprises means for detecting a drop in the AC main below a predetermined level.

When the AC main drops below a predetermined level, the system further comprises means for disabling the second power supply, such that the supplying means provides battery power to the patient monitoring device through the connecting means, and when the patient monitoring device is powered by the battery for a predetermined time period, the system further comprises means for opening the first solid state switch, such that the patient monitoring device is disabled after the predetermined time period.

The system further comprises an alarming means for activating an alarm when one of the anesthesia machine and patient monitoring device is receiving power from the battery, and means for coupling the battery externally to the anesthesia machine, wherein the patient monitoring device is any device capable of receiving auxiliary power, and when the AC mains is available and above a predetermined level, the system further comprises means for recharging the battery.

DETAILED DESCRIPTION OF THE PREFERRED EMBODIMENT

Figure 1:
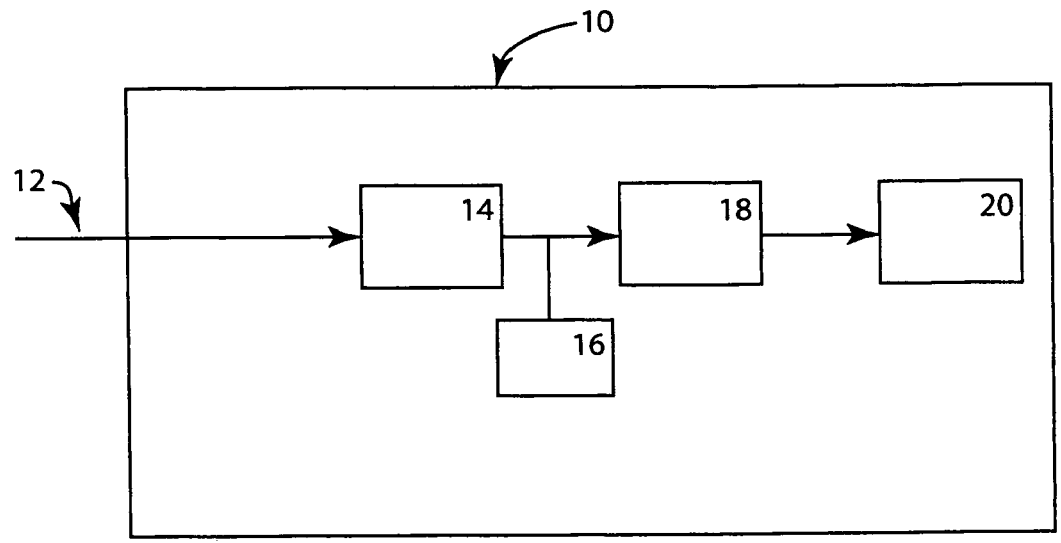
FIG. 1 illustrates a block diagram in accordance with the prior art.
Figure 1:
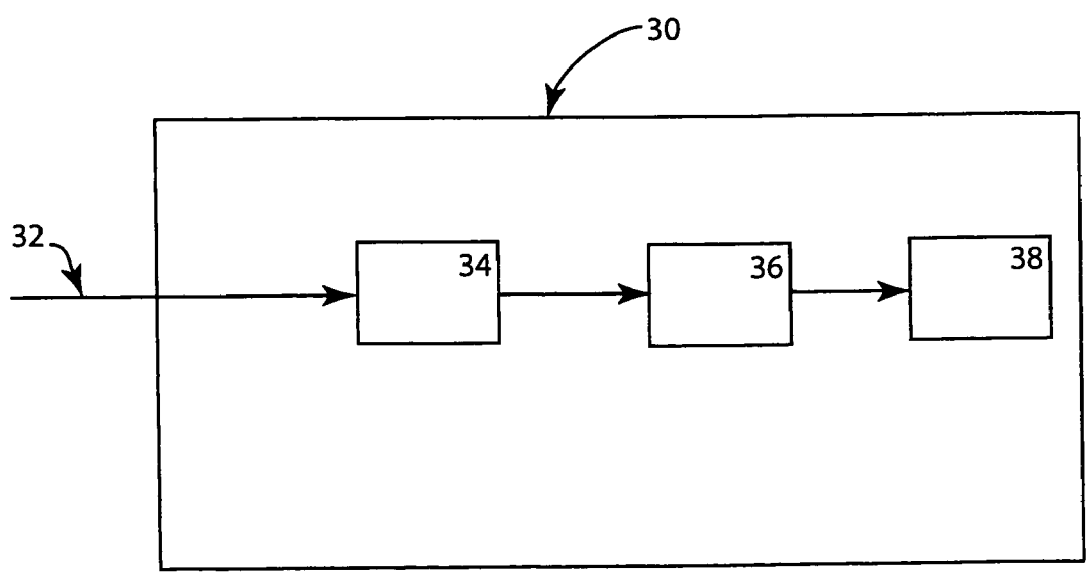
Figure 2:
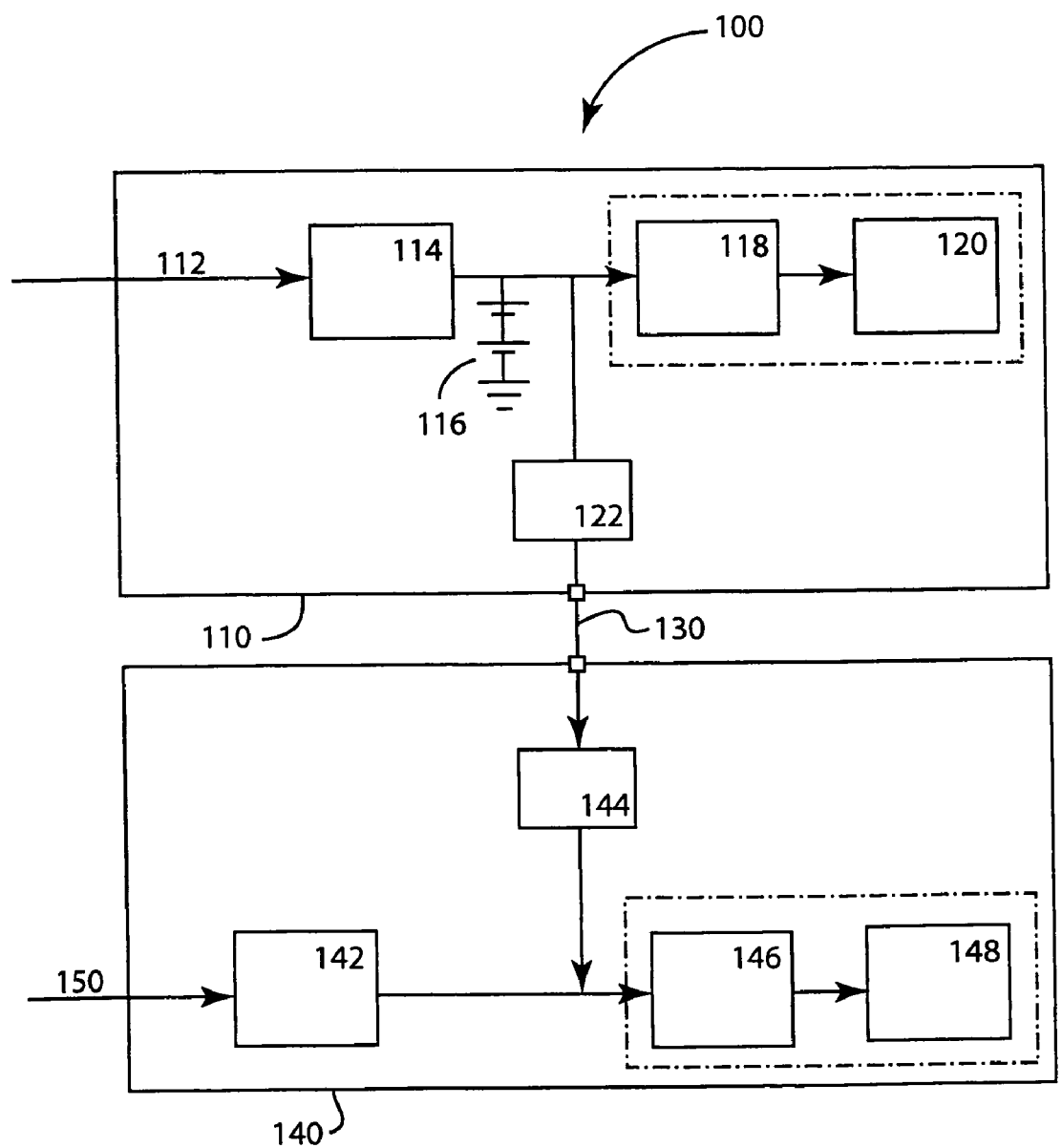
FIG. 2 illustrates a block diagram in accordance with the preferred embodiment of the present invention.

Referring to FIG. 2, the preferred embodiment of the present invention provides a cost effective, multifunctional solution for an integrated anesthesia delivery and patient monitoring system 100 as well as stand-alone applications and other applicable systems known to those skilled in the art. The present invention allows a patient monitoring device 140 and an anesthesia machine 110 to have backed up power in the event of AC mains 112 loss, yet with a cost effective switching power supply 142, that allows the patient monitoring device 140 to be sold separately into hospital care arenas (e.g. critical care) other than the operating room, where the feature of battery backed power is not required. Therefore, the present invention provides auxiliary power to components not required to have such power, while doing so in a cost effective manner.

FIG. 2 depicts a patient monitoring system 100 of the preferred embodiment of the present invention. The integrated system 100 includes an anesthesia machine 110 and a patient monitoring device 140. The anesthesia machine 110 includes a switching power supply 114, a battery 116, a solid state switch 122, a DC/DC converter 118 and an anesthesia machine load 120. The anesthesia machine 110 is provided with an AC mains 112.

The patient monitoring device 140 of the preferred embodiment of the present invention includes an AC to DC converting power supply 142, a solid state switch 144, a DC to DC converter 146 and a patient monitor load 148. In this preferred embodiment, the anesthesia machine 110 and the patient monitoring device 140 are connected by a DC power connection 130. It should be noted that the integrated system 100 depicted in FIG. 2, and described below, is the preferred embodiment of the present invention, and should not serve to limit this invention to exclude other components in place of and in combination with the anesthesia machine 110 and the patient monitoring device 140. In fact, the patient monitoring device 140 could be replaced with any device that is compatible to connect with an auxiliary power source.

Still referring to FIG. 2, if the AC mains 112, 150 is available to both the anesthesia machine 110 and the patient monitoring device 140, both the anesthesia machine 110 and the patient monitoring device 140 operate normally from their respective AC mains 112, 150 power supplies. During normal operation, the first solid state switch 122 is closed, the second solid state switch 144 is open, and no DC power flows through the DC power connection 130 between the anesthesia machine 110 and the patient monitoring device 140.

Still referring to FIG. 2, if AC mains 112 fails during operation, the anesthesia machine 110 continues to operate because it is provided power by the battery 116 through its DC/DC converter 118 to the anesthesia machine load 120. Unlike the prior art systems, if the AC mains 150 also fails while the AC mains 112 has failed, the patient monitoring device 140 is provided power from the battery 116 via the solid state switches 122, 144, and the DC power connection 130 between the anesthesia machine 110 and the patient monitoring device 140, thereby keeping the patient monitoring device 140 operational through its DC/DC converter 146 to the patient monitor load 148.

Additionally, when the AC mains 112, 150 momentarily drops below the operational limit of the patient monitoring device 140 while remaining within the operational limit of the anesthesia machine 110, the power supply PS2, 142, will be disabled. Power from the battery 116 will be sourced from the anesthesia machine 110 through the solid state switches 122, 144 and the DC power connection 130 to the patient monitoring device 140 thereby keeping the patient monitoring device 140 operational. Preferably, the patient monitoring device 140 will be powered in this fashion for a period of one (1) minute. However, other embodiments will allow for this time period to be adjusted according to the needs of the system 100.

When this mode of operation is activated, the anesthesia machine 110 will present an alarm to the user informing them that the patient monitoring device 140 is operating on battery power. This integrated system 100 is designed so that in the unlikely event that the AC mains 112, 150 stays within the operational limit of the anesthesia machine 110, but outside the operational limit of the patient monitoring device 140 for longer than the preferred embodiment time frame of one minute, the patient monitoring device 140 will be disabled to preserve available battery 116 for the backup of the anesthesia machine 110.

It should be noted that alternative embodiments may include an internal or external battery 116 to the patient monitoring device 140 and/or the anesthesia machine 110. Furthermore, another device like a cardiovascular ultrasound device or any medical or non-medical device capable of receiving auxiliary power may be substituted for the patient monitoring device 140. The important aspect of the present invention is that the anesthesia machine 110 must have auxiliary power. The desire in the operating room is to back up more devices using the anesthesia machine 110 back up power source.

Figure 3:
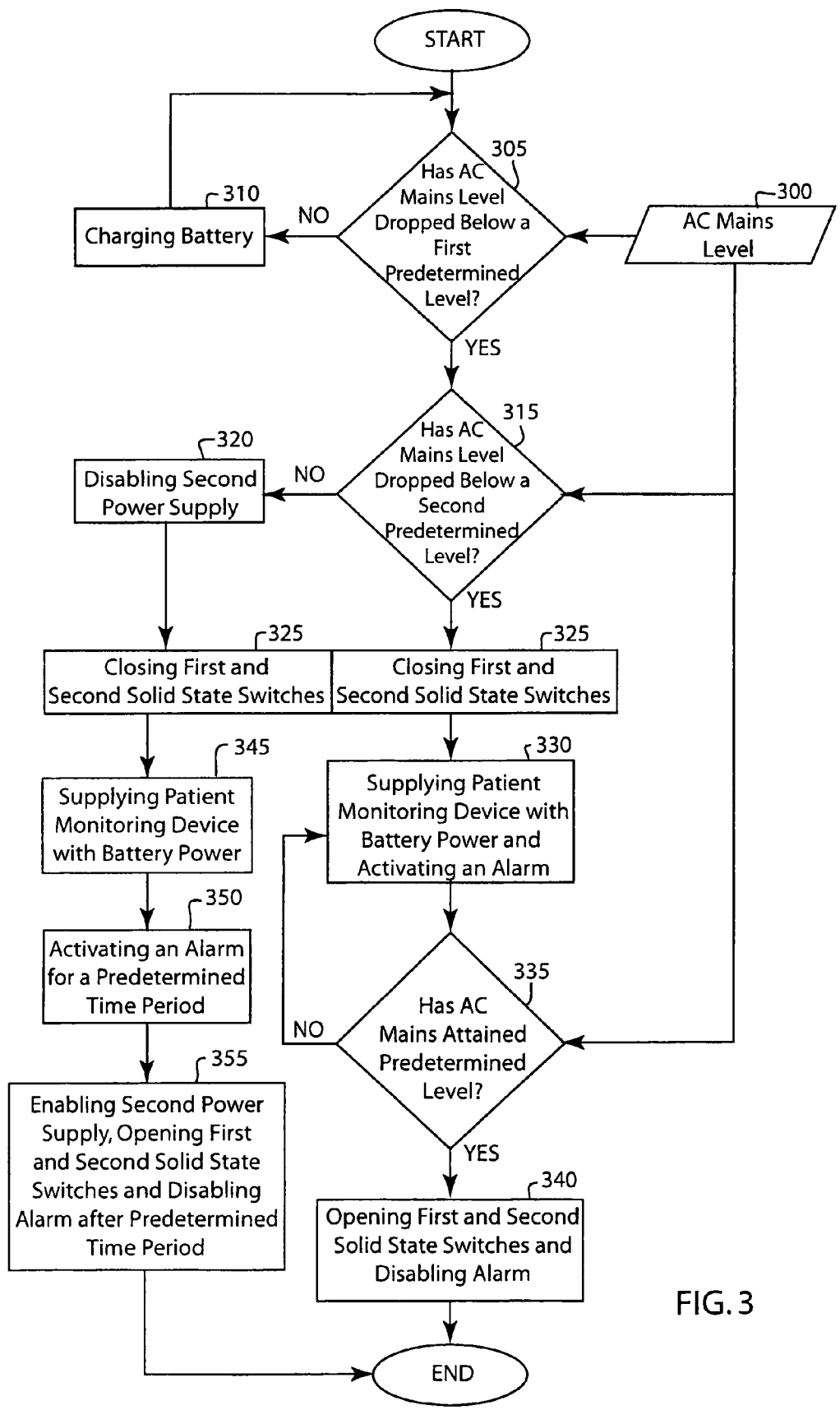
FIG. 3 illustrates a flow chart of a method in accordance with the preferred embodiment of the present invention.

FIG. 3 depicts a flow chart of a method in accordance with the preferred embodiment of the present invention. In step 305, it is determined whether an AC mains level 300 has dropped below a first predetermined operating level for the anesthesia machine and/or the patient monitoring device. If in step 305 it is determined that the AC mains level 300 has not dropped below a predetermined level, then the battery is charged in step 310 and the AC mains level 300 is continuously monitored in step 305.

If in step 305, it is determined that the AC mains level 300 has dropped below a first predetermined level, then in step 315 it is determined whether the AC mains has dropped below a second predetermined operating level for the anesthesia machine.

In step 315, if the AC mains has indeed dropped below the second predetermined level, then in step 325 the first and second solid state switches are closed. It should be noted that if in step 315, the AC mains level is below the second predetermined level, thus disabling the anesthesia machine, but the AC mains remains available to the patient monitoring device, the anesthesia machine will operate from its stand-by battery power. This is normal operational mode and is not depicted in FIG. 3. If in step 315, the AC mains has not dropped below the second predetermined level, then the second power supply is disabled in step 320 before the second solid state switch is closed in step 325. After the second solid state switch is closed in step 325, then the patient monitoring device is supplied with battery power in steps 330 and 345. If the AC mains has not dropped below the second predetermined level, then in step 350, an alarm is activated for a predetermined time period. Thereafter, the battery power supplied to the patient monitoring device in step 345 continues until the predetermined time period in step 350 is completed. In step 355, the second power supply is enabled, the first and second solid state switches are opened and the alarm is disabled after the predetermined time period expires, thus removing battery power from the patient monitoring device.

In step 335, if the AC mains level 300 has not attained a predetermined level, then the monitoring device is continuously supplied with battery power in step 330. If the AC mains 300 has attained a predetermined level in step 335, then the second power supply is enabled (if necessary), the first and second solid state switches are opened and the first alarm is disabled in step 340.

The present invention allows the complete integrated system, including the anesthesia delivery and patient monitoring devices, to remain operational in the event of AC mains loss, and provides a cost effective solution over other alternatives since it provides a battery backup power system that serves a total anesthesia delivery and patient monitoring load without the mains power system for each having to serve the total load. The present invention also allows a patient monitoring system with a narrower AC mains input range to be backed up by an anesthesia delivery system with a wider range input thereby allowing the monitoring system to remain operational, and allows sharing of one battery system without each device needing to have its own battery.

The present invention has been described in terms of specific embodiments incorporated details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

The invention claimed is:

1. A system for providing auxiliary power to an integrated anesthesia delivery and patient monitoring system, the system comprising:
   (a) an anesthesia machine, the anesthesia machine including a battery and a first solid state switch, wherein the first solid state switch is in a normally closed position and the battery is coupled with a first terminal of the first solid state switch;
   (b) a patient monitoring device, the patient monitoring device including a second solid state switch, wherein the second solid state switch is in a normally open position; and
   (c) a DC power connection coupling a second terminal of the first solid state switch of the anesthesia device and the second solid state switch of the patient monitoring device, wherein when an AC mains is unavailable to the patient monitoring device, the second solid state switch closes, such that the battery provides power to the patient monitoring device through the first solid state switch, the second solid state switch and the DC power connection.

2. The system as claimed in claim 1, wherein the anesthesia machine further comprises:
   (a) a first switching power supply; and
   (b) a first DC/DC converter,
      wherein when the AC mains is unavailable to the anesthesia machine, the battery provides power to an anesthesia machine load through the DC/DC converter.

3. The system as claimed in claim 1, wherein the patient monitoring device further comprises:
   (a) a second switching power supply; and
   (b) a second DC/DC converter,
      wherein when the AC mains is unavailable to the patient monitoring device, the battery provides power to a patient monitoring device load through the second DC/DC converter.

4. The system as claimed in claim 3, wherein when the AC mains drops below a predetermined level, the second switching power supply is disabled and the second solid state switch is closed, such that the battery provides power to the patient monitoring device through the DC power connection.

5. The system as claimed in claim 1, wherein the patient monitoring device is powered by the battery for a predetermined time period, further wherein after the predetermined time period, the anesthesia machine will open the first solid state switch, such that the patient monitoring device is disabled.

6. The system as claimed in claim 1, wherein an alarm sounds when one of the anesthesia machine and patient monitoring device is receiving power from the battery.

7. The system as claimed in claim 1, wherein the battery is externally coupled to the anesthesia machine.

8. The system as claimed in claim 1, wherein when the AC mains is available and above a predetermined level, the battery provides no DC power to the anesthesia machine and the patient monitoring device, and the battery is recharged.

9. A method of providing auxiliary power to a carestation, the method comprising:
 (a) monitoring a patient monitoring device for an AC mains failure;
 (b) closing a second solid state switch when the AC mains failure is detected, wherein a second terminal of a first solid state switch and the second solid state switch are connected with a DC power connection, further wherein the first solid state switch is configured in an anesthesia machine and the second solid state switch is configured in the patient monitoring device; and
 (c) supplying the patient monitoring device with DC power from a battery coupled with a first terminal of the first solid state switch in the anesthesia machine through the first solid state switch and the DC power connection.

10. The method as claimed in claim 9, wherein the supplying step further comprises supplying an anesthesia machine load of the anesthesia machine with DC power through a first DC/DC converter when a first switching power supply detects the AC mains failure.

11. The method as claimed in claim 9, wherein the supplying step further comprises supplying a patient monitoring device load of the patient monitoring device with DC power through a second DC/DC converter when a second switching power supply detects the AC mains failure.

12. The method as claimed in claim 11, wherein the detecting step further comprises detecting a drop in the AC main below a predetermined level.

13. The method as claimed in claim 12, wherein when the AC main drops below a predetermined level, the method further comprises:
 (a) disabling the second switching power supply;
 (b) closing the second solid state switch such that the battery provides power to the patient monitoring device through the DC power connection.

14. The method as claimed in claim 9, wherein when the patient monitoring device is powered by the battery for a predetermined time period, the method further comprises the anesthesia machine opening the first solid state switch, such that the patient monitoring device is disabled after the predetermined time period.

15. The method as claimed in claim 9, further comprising activating an alarm when one of the anesthesia machine and patient monitoring device is receiving power from the battery.

16. The method as claimed in claim 9, further comprising coupling the battery externally to the anesthesia machine.

17. The method as claimed in claim 9, wherein when the AC mains is available and above a predetermined level, the method further comprises:
 (a) providing no DC power from the battery to the anesthesia machine and the patient monitoring device; and
 (b) recharging the battery.

18. A system for providing auxiliary power to a carestation, the system comprising:
 (a) means for monitoring a patient monitoring device for an AC mains failure;
 (b) means for connecting an anesthesia machine and the patient monitoring device when the AC mains failure is detected including a first solid state switch and a second solid state switch, wherein a second terminal of the first solid state switch and the second solid state switch are connected with a DC power connection, further wherein the first solid state switch is configured in the anesthesia machine and the second solid state switch is configured in the patient monitoring device; and
 (c) means for supplying the patient monitoring device with DC power from a battery coupled with a first terminal of the first solid state switch in the anesthesia machine through the first solid state switch and the connecting means.

19. The system as claimed in claim 18, wherein the supplying means further comprise means for supplying an anesthesia machine load of the anesthesia machine with DC power through a first DC/DC converter when the monitoring means detects the AC mains failure.

20. The system as claimed in claim 18, wherein the supplying means further comprises means for supplying a patient monitoring device load of the patient monitoring device with DC power through a second DC/DC converter when the monitoring means detects the AC mains failure.

21. The system as claimed in claim 20, wherein the monitoring means further comprises means for detecting a drop in the AC main below a predetermined level.

22. The system as claimed in claim 21, wherein when the AC main drops below a predetermined level, the system further comprises means for disabling the detecting means, such that the supplying means provides battery power to the patient monitoring device through the connecting means.

23. The system as claimed in claim 18, wherein when the patient monitoring device is powered by the battery for a predetermined time period, the system further comprises means for opening the first solid state switch, such that the patient monitoring device is disabled after the predetermined time period.

24. The system as claimed in claim 18, further comprising an alarming means for activating an alarm when one of the anesthesia machine and patient monitoring device is receiving power from the battery.

25. The system as claimed in claim 18, further comprising means for coupling the battery externally to the anesthesia machine.

26. The system as claimed in claim 18, wherein when the AC mains is available and above a predetermined level, the system further comprises means for recharging the battery.

* * * * *